United States Patent [19]
Frohn et al.

[11] Patent Number: 5,912,358
[45] Date of Patent: Jun. 15, 1999

[54] PROCESS FOR PREPARING 2-PYRROLIDONES

[75] Inventors: Lutz Frohn, Erkrath; Jörg-Dietrich Jentsch, Mülheim; Eberhard Zirngiebl, Cologne, all of Germany

[73] Assignee: Bayer Aktiengesellschaft, Leverkusen, Germany

[21] Appl. No.: 08/656,001

[22] Filed: May 24, 1996

[30] Foreign Application Priority Data

Jun. 2, 1995 [DE] Germany ............... 19520258

[51] Int. Cl.⁶ .................................................. C07D 207/267
[52] U.S. Cl. ............................................. 548/543; 548/554
[58] Field of Search ................................ 548/554, 552, 548/543

[56] References Cited

U.S. PATENT DOCUMENTS

| | | | |
|---|---|---|---|
| 3,884,936 | 5/1975 | Hollstein | 548/554 |
| 4,157,989 | 6/1979 | Antos | 252/441 |
| 4,420,620 | 12/1983 | Murib | 548/554 |
| 4,800,227 | 1/1989 | Matson | 548/543 |
| 5,157,127 | 10/1992 | Weyer et al. | 548/552 |
| 5,276,165 | 1/1994 | Weyer et al. | 548/554 |
| 5,434,273 | 7/1995 | Weyer et al. | 548/554 |
| 5,478,950 | 12/1995 | Bergfeld et al. | 548/552 |

FOREIGN PATENT DOCUMENTS

| | | |
|---|---|---|
| 0 105 663 A3 | 4/1984 | European Pat. Off. . |
| 0 147 219 A3 | 7/1985 | European Pat. Off. . |
| 0 166 619 A3 | 1/1986 | European Pat. Off. . |
| 0 361 484 A3 | 4/1990 | European Pat. Off. . |
| 0460474 | 12/1991 | European Pat. Off. . |
| 0 545 150 A1 | 6/1993 | European Pat. Off. . |
| 2 200 600 | 8/1972 | Germany . |
| 2445871 | 4/1975 | Germany . |
| 212181 | 2/1984 | Switzerland . |
| 1439558 | 6/1976 | United Kingdom . |
| 1 439 558 | 6/1979 | United Kingdom . |

OTHER PUBLICATIONS

Chemical Abstracts, Vo. 101, p. 687, abstract No. 171086r, abstract of CS212,181 (1984).

*Primary Examiner*—Johann Richter
*Assistant Examiner*—Laura R. C. Lutz
*Attorney, Agent, or Firm*—Sprung Kramer Schaefer & Briscoe

[57] ABSTRACT

2-Pyrrolidones can be prepared by simultaneous reaction of maleic acid, ammonia or a primary amine and hydrogen at elevated temperature and elevated pressure in the liquid phase over a supported catalyst, with the supported catalyst containing both palladium and rhenium in metallic or bound form.

13 Claims, No Drawings

PROCESS FOR PREPARING 2-PYRROLIDONES

BACKGROUND OF THE INVENTION

1. Field of the Invention

The present invention relates to a process for preparing 2-pyrrolidones by simultaneous reaction of maleic anhydride, ammonia or a primary amine and hydrogen at elevated temperature and elevated pressure in the liquid phase, using a supported catalyst containing both palladium and rhenium in metallic or bound form.

2-Pyrrolidone and, in particular, N-substituted 2-pyrrolidones are important polar solvents and extractants, for example solvents for polymers such as polyurethanes, polyimides, polyamides, polyarylene sulphides, and extractants for, for example, acetylene, butadiene, aromatics. Such pyrrolidones are also much-used media for chemical reactions (Ullmann, 4th edition, Vol. 19, Verlag Chemie 1980, p. 641–642).

2. Description of the Related Art

Maleic anhydride (MA) can be converted by hydrogenation, for instance using catalytically activated hydrogen, into succinic anhydride which can form the open-chain succinic acid in the presence of water. Furthermore, MA can be converted by hydrogenation directly or via the succinic anhydride stage into γ-butyrolactone which can form the open-chain ω-hydroxybutyric acid in the presence of water. It is also possible to convert the γ-butyrolactone into 2-pyrrolidone or into N-substituted 2-pyrrolidones by means of ammonia or primary amines. It is also possible to react MA with ammonia or primary amines in the presence of catalytically activated hydrogen to directly form 2-pyrrolidone or N-substituted 2-pyrrolidones.

The wide variety of possible reactions mentioned for MA and its downstream products, which compete with one another, make it probable that all these products are formed as a mixture if MA is simultaneously reacted with ammonia or primary amines and catalytically activated hydrogen. There have therefore been many attempts to achieve a very high selectivity in respect of the, optionally N-substituted, 2-pyrrolidones by the selection of suitable catalysts and by the gradual attainment of the individual reaction stages, which are then reacted further in steps.

CS 212 181 describes a preparation process for N-alkyl-2-pyrrolidones in which MA or succinic anhydride and a primary amine are first converted into the N-alkyl-monoamide of maleic or succinic acid which is cyclized over a hydrogenation catalyst to give the N-alkylpyrrolidone. Hydrogenation catalysts mentioned are those containing elements of groups I, II, V, VII and VIII of the Periodic Table (Mendeleev). Examples of such catalysts are Cu—Zn, Cu—Zn—Cr, Raney Ni, Raney Co; an example of a noble metal catalyst which is described is a mixed catalyst consisting of 1 g of Pt (0.2% by weight)-Re (0.1% by weight) on γ-$Al_2O_3$, 6 g of Raney Cu and 3 g of Raney Co.

In the search for a stable catalyst, German Offenlegungsschrift 24 45 871 describes a process for preparing 2-pyrrolidone in which MA is reacted with ammonia or the diammonium salt of succinic acid and, in each case, with hydrogen using a catalyst containing Ni and Re and/or Mo. The ratio of Ni to Re or Mo is 1:0.001–0.25.

A further process for preparing N-substituted 2-pyrrolidones likewise starts from maleic anhydride, maleic acid and/or fumaric acid, a primary amine and hydrogen, which are reacted in the presence of a catalyst containing Co and at least one of the elements Mn, Cu, P, Mo and/or Na (EP 460 474). This process is carried out in the presence of a solvent at elevated temperature and at elevated pressure.

Still another process for preparing N-substituted 2-pyrrolidones likewise starts from MA or maleic acid which are reacted with a primary amine in the presence of catalytically activated hydrogen. This process is further distinguished by the primary amine being able to be used in admixture with the associated secondary and/or tertiary amines and the process being carried out in the presence of water and/or ammonia. The catalyst used contains at least one element of transition groups I, VII or VIII of the Periodic Table (Mendeleev) and can additionally contain elements of transition group VI. The catalysts used in the examples are: Cu—$Al_2O_3$ and Co—Cu—Mn—Mo—Na—$H_3PO_4$.

U.S. Pat. No. 4,800,227 describes the preparation of 2-pyrrolidone or its N-substituted derivatives by reaction of MA with ammonia or primary amines and catalytically activated hydrogen. Use is made of catalysts containing palladium and, on a separate support, at least one element from the group consisting of ruthenium, rhodium and rhenium. The examples describe the use of a catalyst mixture which has been prepared from Ru(5%)/$Al_2O_3$ and Pd(5%)/$Al_2O_3$ in powder form by mixing. These two catalyst fractions are added to one another in various ratios by simple mixing. The process is carried out in a polar liquid reaction medium such as water, tetrahydrofuran or dioxane.

The patent specifications mentioned show the great sensitivity of the basic reaction towards the catalyst used. Most documents indicate that base metal catalysts, such as Raney Ni, are used more frequently than noble metal catalysts; in cases where both base metal catalysts and noble metal catalysts are used, the base metal catalyst represents the predominant proportion. When using more than one noble metal, for instance as described in U.S. Pat. No. 4,800,277, it appears important to use these metals separately from one another on different support particles.

SUMMARY OF THE INVENTION

It has now been found that a supported catalyst containing both Pd and Re together on one support is particularly favourable in the preparation of, optionally N-substituted, 2-pyrrolidones. It is here possible to refrain from using solvents foreign to the system when working in the liquid phase, which enables particularly high space-time yields to be achieved. It has further been found that the possible by-product γ-butyrolactone is not formed or formed only to a subordinate degree. It has further been found that tetrahydrofuran which is formed by over-hydrogenation over Pd/Ru catalysts is likewise not formed or formed only to a subordinate degree according to the invention.

The invention provides a process for preparing 2-pyrrolidones of the formula

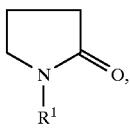

(I)

where

R$^1$ is hydrogen, straight-chain or branched C$_1$–C$_{20}$-alkyl, C$_3$–C$_8$-cycloalkyl or C$_7$–C$_{10}$-aralkyl, which is characterized in that maleic anhydride, a primary amine of the formula

R$^1$—NH$_2$ (II), where

R$^1$ is as defined above, and hydrogen are simultaneously reacted with one another batchwise or continuously at from 150 to 330° C. and from 10 to 300 bar in the liquid phase over a supported catalyst containing both palladium and rhenium in metallic or bound form, with palladium being present in an amount of from 0.5 to 15% by weight and rhenium being present in an amount of from 0.5 to 10% by weight and the sum of the two metals being from 2 to 15.5% by weight, all calculated as metal and based on the total weight of the supported catalyst.

DETAILED DESCRIPTION OF THE INVENTION

Straight-chain or branched C$_1$–C$_{20}$-alkyl is, for example, methyl, ethyl, propyl, isopropyl, butyl, isobutyl, tert-butyl, the isomeric pentyls, hexyls, octyls, decyls, dodecyls, tetradecyls, hexadecyls, octadecyls and eicosyls.

C$_3$–C$_8$-Cycloalkyl is, for example, cyclopropyl, cyclobutyl, cyclopentyl, cyclohexyl, cycloheptyl, cyclooctyl and (poly)methyl and (poly)ethyl derivatives thereof having a maximum of 8 carbon atoms.

C$_7$–C$_{10}$-Aralkyl is, for example, benzyl, α-phenyl-ethyl, β-phenyl-ethyl, phenyl-propyl or phenyl-butyl.

Preferably, the primary amines reacted have the formula

R$^{11}$—NH$_2$ (III)

where

R$^{11}$ is hydrogen, straight-chain or branched C$_1$–C$_{10}$-alkyl or benzyl.

Particularly preferably, the primary amines reacted have the formula

R$^{21}$—NH$_2$ (IV)

where

R$^{21}$ is hydrogen, methyl or straight-chain or branched octyl.

Primary amines of the specified type are known to those skilled in the art and are available in industry in large amounts. For the purposes of the invention, ammonia is regarded as a primary amine (R$^1$ or R$^{11}$ or R$^{21}$=H).

Maleic anhydride (MA) can be used either in pure form or in the form which is obtained industrially by oxidation of butane, butene or benzene.

Hydrogen can be used either in pure form or in the form of an industrially available tail gas as is obtained, for instance, in petrochemical plants (H$_2$ content: at least 70% by volume, remainder to 100%: methane, ethane and other known impurities).

The process of the invention is characterized by the use of a supported catalyst containing both palladium and rhenium in metallic or bound form. Suitable supports are, for example: carbon in various forms, SiO$_2$ or Al$_2$O$_3$ in various forms, aluminosilicates, zeolites, metal oxides such as ZrO$_2$, TiO$_2$, ZnO, pumice, phosphates and other supports known to those skilled in the art for hydrogenation catalysts.

The catalyst to be used according to the invention contains both palladium and rhenium as active constituents. It has been found that it is important not to use a mixture of different catalysts each of which contains either palladium or rhenium, but to have both active constituents present together on one support. The amount of palladium is from 0.5 to 15% by weight, preferably from 1 to 12% by weight; the amount of rhenium is from 0.5 to 10% by weight, preferably from 1 to 8% by weight; the total amount of both active constituents is from 2 to 15.5% by weight, preferably from 3 to 13% by weight. All weights are calculated as metal and based on the total weight of the supported catalyst. The active constituents are generally applied to the support in the form of metal compounds, but when the catalyst is used are obviously predominantly present in metallic form, which applies at least to the palladium. It is assumed, without specific studies having been made on this subject, that the rhenium in the direct spatial vicinity on the catalyst support has a pronounced activity- and selectivity-promoting action on the palladium. This activity- and selectivity-promoting action is distinctly beyond that of the other cocatalysts, for example beyond that of ruthenium which, particularly when present alone on one support, shows a strong tendency towards over-hydrogenation.

The invention further provides the above-described catalyst.

Preferred supports are carbon, Al$_2$O$_3$, SiO$_2$ or ZrO$_2$ in various forms. Thus, carbon can be used either as graphite or as activated carbon in the form of pieces or powder. Carbon as catalyst support can have internal surface areas of from 50 to 2000 m$^2$/g, activated carbons specifically from 400 to 2000 m$^2$/g. Al$_2$O$_3$ as catalyst support generally has from 50 to 350 m$^2$/g. SiO$_2$ as catalyst support generally has from 50 to 600 m$^2$/g. ZrO$_2$ as catalyst support generally has from 50 to 200 m$^2$/g. Particular preference is given to using carbon, very particularly preferably activated carbon having the specified internal surface areas.

In general, either palladium or rhenium can be present in excess over the other on the catalyst to be used according to the invention. However, it is preferred that palladium is present in excess over rhenium. The weight ratio Pd:Re may be from 1.5 to 10:1, preferably 2–6:1.

To prepare the catalyst to be used according to the invention, the support can be impregnated or sprayed, for example with an aqueous, optionally acid aqueous or alcoholic solution of a Pd salt, for example PdCl$_2$, (NH$_4$)$_2$[PdCl$_4$], PdSO$_4$ or Pd(NO$_3$)$_2$. The Pd is subsequently precipitated by means of aqueous alkali metal hydroxide (for example sodium hydroxide solution) as oxide or hydroxide and thus fixed to the support. The Pd-containing support is subsequently further impregnated or sprayed with the aqueous or alcoholic solution of a Re compound, for example with a solution of ReCl$_3$, ReCl$_4$, ReO$_2$, ReO$_3$, Re$_2$O$_7$. It has been found to be advantageous to fix the Re to the support by removing the solvent used for application of the Re compounds by simple drying. Subsequent to the application of the two active constituents to the support, these can be reduced, for example using hydrogen, carbon monoxide, hydrazine or formaldehyde. However, it is equally possible to allow this reduction to proceed during the course of the process of the invention. This converts at least the Pd into the metallic state.

The process of the invention is carried out in the liquid phase at a temperature of from 150 to 330° C., preferably from 200 to 320° C., particularly preferably from 240 to 300° C., and elevated pressure of from 10 to 300 bar, preferably from 50 to 200 bar, particularly preferably from 70 to 150 bar. The elevated pressure is essentially that of the injected $H_2$, for example in pure form or in the above-described form having an $H_2$ content of at least 70% by volume; however, it is also possible to additionally use an inert gas such as nitrogen or an inert lower hydrocarbon such as methane or ethane. In any case, the hydrogen is used in excess, for example in from 2 to 1000 times the stoichiometrically required amount. MA and the primary amine are used in a molar ratio of 0.1–10:1, preferably 0.2–5:1. The molar ratio is selected primarily on the basis of an economic point of view: thus, an excess of the cheaper chemical is used, so as to utilize the more expensive chemical to the best possible extent. For example, in the case of expensive primary amines, the relatively cheap MA is used in excess; unreacted MA can be recovered and recycled to the reaction. On the other hand, the cheap ammonia can be used in excess and be recovered after the reaction.

The process of the invention can be carried out batchwise or continuously, for example in an autoclave or in a pressure-resistant tube unit providing a residence time for the reaction mixture.

If solvents are used, it is possible to use virtually all solvents which are inert under the reaction conditions, e.g. water, aliphatic and aromatic hydrocarbons such as pentane, hexane, heptane, octane, benzene, toluene or xylene, ethers such as diethyl ether, diisopropyl ether, methyl tert-butyl ether, dioxane or tetrahydrofuran or mixtures of these solvents. Use can also advantageously be made of N-substituted and N-unsubstituted pyrrolidones, for example NMP and 2-pyrrolidone, as solvent.

EXAMPLES

Example 1

Catalyst Preparation 50 g of pulverulent activated carbon (Norit) were slurried in 300 ml of twice-distilled water. 13.5 g (60 mmol) of palladium acetate and 2.0 g (4.1 mmol) of $Re_2O_7$ were added, the reaction mixture was left stirring for 24 hours at 20° C. and was then evaporated to dryness at 70° C. and 10 mbar on a rotary evaporator. Drying for 12 hours at 120° C. in a drying oven gave 62.6 g of catalyst containing 9.7% by weight of Pd, 2.3% by weight of Re and 2% by weight of water.

Example 2

Catalyst Preparation 20 g of pulverulent γ-$Al_2O_3$ (Rhône-Poulenc) were slurried in 120 ml of twice-distilled water. 7.2 g (10.1 mmol) of an aqueous $Na_2PdCl_4$ solution containing 15% by weight of Pd were added, the mixture was left stirring for a further 30 minutes and the pH was adjusted to 8 using 5% strength NaOH. 6 ml of 20% strength aqueous hydrazine solution were added, the mixture was left stirring for a further 30 minutes and the catalyst was washed chloride-free on a suction filter. The moist filter cake was slurried in 120 ml of twice-distilled water and admixed with 0.9 g of $Re_2O_7$ (1.9 mmol) dissolved in 5 ml of twice-distilled water. The reaction mixture was stirred for a further 30 minutes and then evaporated to dryness at 70° C. and 10 mbar on a rotary evaporator. Drying for 12 hours at 120° C. in a drying oven gave 23.4 g of catalyst containing 5.4% by weight of Pd and 3.6% by weight of Re.

Example 3

In an autoclave, 49.5 g (0.5 mol) of MA, 100 g of $H_2O$, 39 g of aqueous methylamine solution (40% by weight) and 5 g of suspension catalyst (9.7% of Pd and 2.3% of Re on carbon support) were intensively contacted at 275° C. and 120 bar with hydrogen. After 4 hours, the experiment was stopped and the contents of the autoclave were analyzed by gas chromatography. The yield of NMP achieved was 67%.

Example 4

Example 3 was repeated using 5 g of catalyst containing 5.4% of Pd and 3.6% of Re on $Al_2O_3$ as support in place of the catalyst indicated in Example 3. The yield of NMP was 69%.

Example 5

Example 3 was repeated using 5 g of catalyst containing 9.7% of Pd and 2.3% of Re on $Al_2O_3$ as support in place of the catalyst indicated in Example 3. The yield of NMP was 62%.

Example 6

Example 3 was repeated using 5 g of catalyst containing 2% of Pd and 5% of Re on $Al_2O_3$ as support in place of the catalyst indicated in Example 3. The yield of NMP was 64%.

Example 7

Example 3 was repeated using 5 g of catalyst containing 5.4% of Pd and 3.6% of Re on $Al_2O_3$ as support in place of the catalyst indicated in Example 3. The yield of NMP was 68%.

Comparative Example 1

Example 3 was repeated using 5 g of catalyst containing 9.7% of Pd on a carbon support in place of the catalyst indicated in Example 3. The yield of NMP was 25%.

Comparative Example 2

Example 3 was repeated using 5 g of catalyst containing 2.3% of Re on a carbon support in place of the catalyst indicated in Example 3. No NMP could be detected.

Comparative Example 3

Example 3 was repeated using 2.5 g of catalyst containing 9.7% of Pd on a carbon support and a further 2.5 g of catalyst containing 2.3% of Re on a separate carbon support in place of the catalyst indicated in Example 3. The yield of NMP was 56%.

What is claimed is:

1. A process for preparing a 2-pyrrolidone of the formula

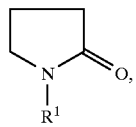

where
  $R^1$ is straight-chain or branched $C_1$–$C_{20}$-alkyl, $C_3$–$C_8$-cycloalkyl or $C_7$–$C_{10}$-aralkyl,
wherein maleic anhydride, a primary amine of the formula $R^1$—$NH_2$, where
  $R^1$ is as defined above,
and hydrogen are simultaneously reacted with one another batchwise or continuously at from 150 to 330° C. and from 10 to 300 bar in the liquid phase over a supported catalyst containing both palladium and rhenium in metallic or bound form, with palladium being present in an amount of from 0.5 to 15% by weight and rhenium being present in an amount of from 0.5 to 10% by weight and the sum of the two metals being from 2 to 15.5% by weight, all calculated as metal and based on the total weight of the supported catalyst.

2. The process of claim 1, wherein the primary amine reacted has the formula $R^{11}$—$NH_2$ where
  $R^{11}$ is straight-chain or branched $C_1$–$C_{10}$-alkyl, cyclopropyl, cyclopentyl, cyclohexyl or benzyl.

3. The process of claim 2, wherein the primary amine reacted has the formula $R^{21}$—$NH_2$ where
  $R^{21}$ is methyl or octyl.

4. The process of claim 1, which is carried out at from 200 to 320° C.

5. The process of claim 4, which is carried out at from 240 to 300° C.

6. The process of claim 1, which is carried out at from 50 to 200 bar.

7. The process of claim 6, which is carried out at from 70 to 150 bar.

8. The process of claim 1, wherein palladium is present in an amount of from 1 to 12% by weight and rhenium is present in an amount of from 1 to 8% by weight and the sum of the two metals is from 3 to 13% by weight, all calculated as metal and based on the total weight of the supported catalyst.

9. The process of claim 1, wherein palladium and rhenium are present in a weight ratio of Pd:Re=1.5–10:1.

10. The process of claim 9, wherein palladium and rhenium are present in a weight ratio of Pd:Re=2–6:1.

11. The process of claim 1, wherein the support used is carbon, $Al_2O_3$, $ZrO_2$ or $SiO_2$.

12. The process of claim 11, wherein the support used is carbon having an internal surface area of from 50 to 2000 $m^2/g$.

13. The process of claim 12, wherein the support used is activated carbon having an internal surface area of from 400 to 2000 $m^2/g$.

* * * * *

UNITED STATES PATENT AND TRADEMARK OFFICE
CERTIFICATE OF CORRECTION

PATENT NO.   : 5,912,358
DATED        : June 15, 1999
INVENTOR(S)  : Lutz FROHN, et al.

It is certified that error appears in the above-identified patent and that said Letters Patent is hereby corrected as shown below:

Title Page: "References Cited"    "Foreign Patent Documents"
Reference 212181, 2/1984, Switzerland,
should read 212181, 2/1984, Czech.

Signed and Sealed this

Fourth Day of January, 2000

Attest:

Attesting Officer

*Acting Commissioner of Patents and Trademarks*